United States Patent
Frigg

Patent Number: 5,295,991
Date of Patent: Mar. 22, 1994

[54] SURGICAL INSTRUMENT FOR POSITIONING OSTEOSYNTHETIC ELEMENTS

[75] Inventor: Robert Frigg, Davos-Platz, Switzerland

[73] Assignee: Synthes (U.S.A.), Paoli, Pa.

[21] Appl. No.: 883,177

[22] Filed: May 15, 1992

[30] Foreign Application Priority Data

May 24, 1991 [CH] Switzerland ............ 01543/91-2

[51] Int. Cl.⁵ .................................. A61B 17/56
[52] U.S. Cl. .................................. 606/62; 606/64
[58] Field of Search ............. 606/60, 61, 62, 63, 606/64, 65, 66, 67, 96, 97, 98

[56] References Cited

U.S. PATENT DOCUMENTS

| | | | |
|---|---|---|---|
| 4,281,649 | 8/1981 | Derweduwen | 606/64 |
| 4,622,959 | 11/1986 | Marcus | 606/64 |
| 4,667,664 | 5/1987 | Taylor | 606/64 |
| 4,817,591 | 4/1989 | Klaue | 606/64 |
| 4,846,162 | 7/1989 | Moehring | 606/64 |
| 4,862,883 | 9/1989 | Freeland | 606/64 |
| 4,877,019 | 10/1989 | Vives | 606/64 |
| 4,911,153 | 3/1990 | Border | 606/64 |
| 4,913,137 | 4/1990 | Azer | 606/64 |
| 5,100,404 | 3/1992 | Hayes | 606/64 |

*Primary Examiner*—Michael A. Brown
*Attorney, Agent, or Firm*—Davis Hoxie Faithfull & Hapgood

[57] ABSTRACT

A surgical instrument for treating fractures of the neck and shaft of the femur has a frame attachable to an intramedullary pin inserted in the medulla and bearing a drill jig for inserting screws into the femur head.

16 Claims, 8 Drawing Sheets

SURGICAL INSTRUMENT FOR POSITIONING OSTEOSYNTHETIC ELEMENTS

FIELD OF THE INVENTION

The invention refers to a surgical instrument for positioning osteosynthetic elements particularly in the treatment of fractures of the femur.

BACKGROUND OF THE INVENTION

In the operative treatment of fractures of the femur, combination fractures of the femur neck and shaft cause the greatest problems, because of the incompatible osteosynthetic procedures for these two different types of fractures.

In the current state of the art, femur shaft fractures are immobilized with intramedullar nails or pins. Femur-neck fractures are immobilized with angular plates, hip screws, or by means of three screws inserted in parallel. In younger patients the screw method is the principal method used, because this type of treatment causes the least additional damage to the femur neck.

As regards the urgency with which the two fractures must be immobilized, treating the femur neck fracture is the most immediate. With this type of fracture there is a danger that if it is not immobilized, a circulatory disturbance will occur in the femur head. Most such circulatory disturbances end in a resection of the femur head and the installation of a full prosthesis. In contrast to this complication, a delay in treating a fracture in the femur shaft is easier to deal with. Nevertheless, use of intramedullary implants for immobilizing this type of combination fracture is becoming increasingly frequent. Such intramedullary nails or pins have at their proximal end cross-holes for screws to be inserted laterally through the intramedullary pin into the femur head.

The screws needed for immobilizing the femur-neck fracture have a diameter of at least 6.5 mm., and are inserted in parallel fashion into the femur head. Because of the intramedullary pin, these screws can be inserted only one below the other, and so only two screws can be inserted through the pin into the femur head.

To ensure that the intramedullary pin is not too greatly weakened by the two cross-holes and the additional conveying of force via the screws, the intramedullary pin is made larger in diameter than would otherwise be used. This larger diameter requires a larger drilling of the medulla, which is out of proportion to the shaft fracture to be immobilized.

However, the principal disadvantage of this osteosynthetic procedure is that the shaft fracture is treated first, before the femur-neck fracture can be stabilized. The disadvantage of this method becomes particularly apparent when we realize the amount of force needed to drive in an intramedullary pin. Every blow needed to drive in the pin further separates the fracture in the neck area, which inevitably threatens the blood supply in the femur head area.

SUMMARY OF THE INVENTION

The invention provides assistance with this problem. In accordance with the invention, there is provided a surgical instrument for positioning osteosynthetic attachment elements, such as bone screws or bone pins, in any position relative to an intramedullary pin or a manipulative intramedullary pin. In particular, it facilitates the inserting of bone screws in front of or behind the intramedullary pin, at an angle to the pin axis, which can be chosen at will.

Specifically, the invention comprises a surgical instrument for positioning osteosynthetic elements comprising a U-shaped frame having a first end and a second end, anchoring means at said first end for attachment to an intramedullary nail and adjustable retaining means at said second end for receiving a drill jig.

The advantages achieved through the invention consist essentially in the fact that thanks to a surgical instrument according to the invention, and despite the use of an intramedullary pin, the primary immobilization of a femur-neck fracture is facilitated, which immobilization is achieved through screwing the femur head independently of intramedullary pins. Another advantage is that holes can be drilled at any desired height at any desired angle with respect to the intramedullary pin position, without fear that the intramedullary pin will be affected.

BRIEF DESCRIPTION OF THE DRAWINGS

One embodiment of the invention is illustrated in the drawings in which.

DETAILED DESCRIPTION OF A SPECIFIC EMBODIMENT

Figure 1:
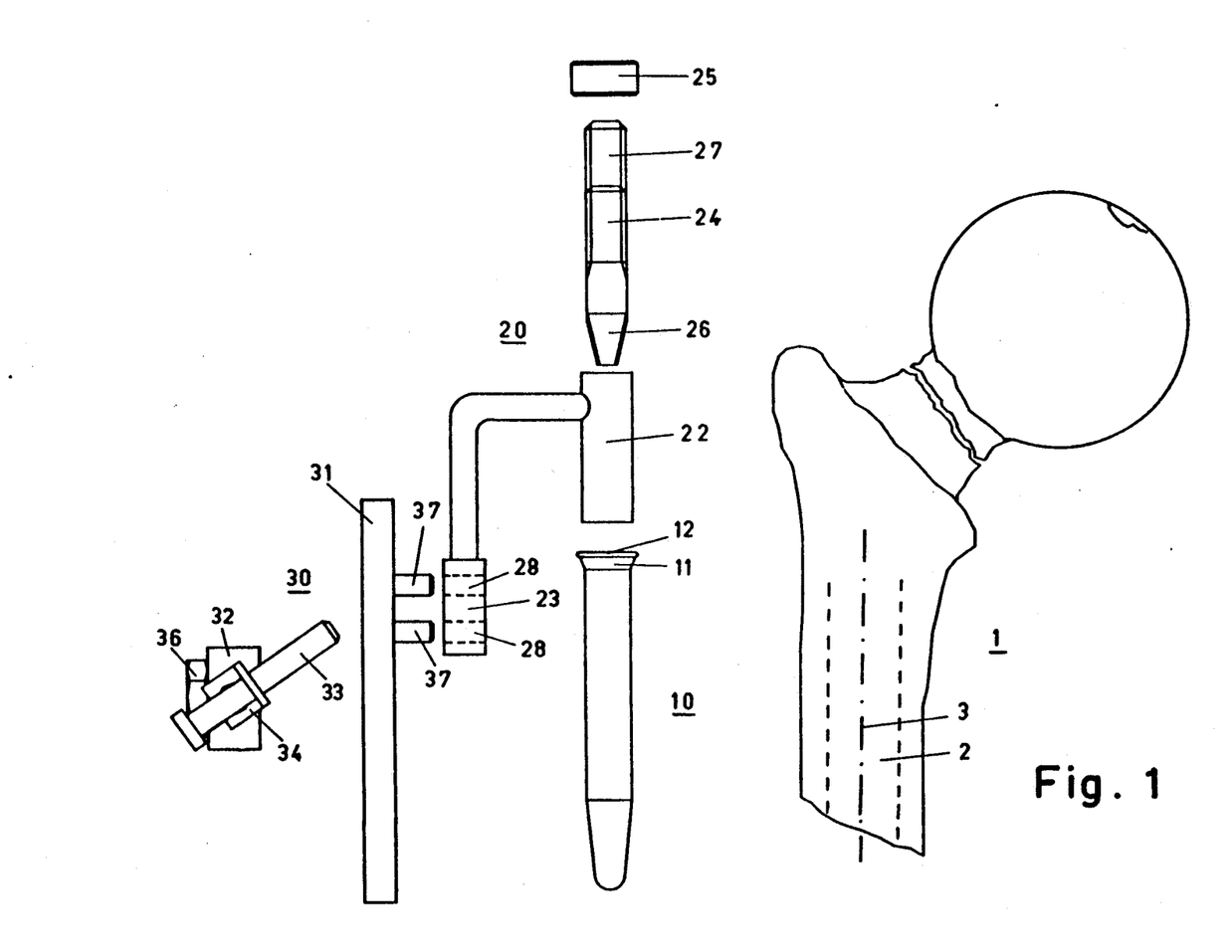
FIG. 1 is a schematic view in side elevation of a device according to the invention, in disassembled state, for use on the femur.
Figure 2:
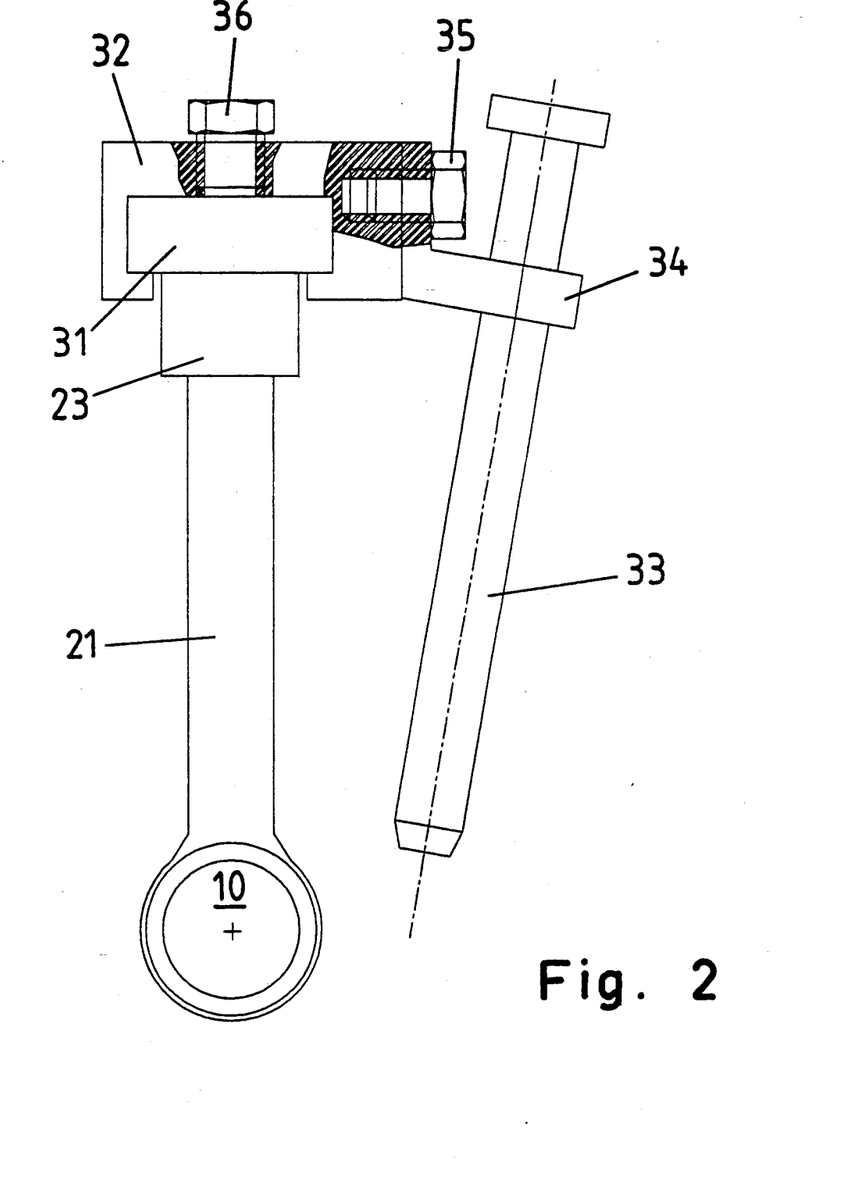
FIG. 2 is a bottom plan view, partly in horizontal section, of the manipulative intramedullary pin with a device according to the invention in assembled state.

Referring to FIGS. 1 and 2, a surgical instrument according to the invention comprises a U-shaped frame 20 to which may be attached a drill jig 30. The frame 20 has a first end or leg 22 for connection with a manipulative intramedullary pin 10, and a second end or leg 23 for connection to the drill jig 30. The term "manipulative intramedullary pin (or nail)" is used here to identify an intramedullary pin designed primarily to assist the surgeon in various manipulative techniques, in distinction to an intramedullary nail implanted primarily for its own therapeutic value. As shown in FIG. 1 the manipulative intramedullary pin 10 can be inserted into the medullary canal 2 of a tubular bone 1 and the frame can be separably, coaxially connected to the pin 10.

The manipulative intramedullary pin 10 is smaller than the medullar pin customarily used for implants. Typically, its external diameter is a maximum of 12 mm, and it is 90 mm long (often 80 mm long and a diameter of 9 mm). This size is completely adequate for the desired purpose of an unambiguous determination of the longitudinal axis 3 of medullary canal 2 and the creation of a reference axis for the frame 20 and the drill jig 30. The intramedullary pin 10 has at its proximal end 11 an attachment means 12, in the form of a conical socket with internal threading, for the purpose of separable attachment of frame 20.

Frame 20 comprises a basic U-shaped impact frame 21 (FIG. 3—useful for inserting an intramedullary pin) having a medullary pin end or leg 22 and a drill-jig end or leg 23. A conical bolt 24 and a nut 25 are provided for connecting leg 22 to an intramedullary pin. The leg 22 of the impact frame 21 is formed as a hollow cylinder that can accept the bolt 24 and anchor the frame to an intramedullary pin. The drill-jig leg 23 has a connection element 28 for attachment of the drill jig 30. In the embodiment shown, the connection element 28 has two holes or channels that serve simultaneously for attachment of the drill jig and as a guide and drill jig for the emplacement of locking screws.

Figure 3:
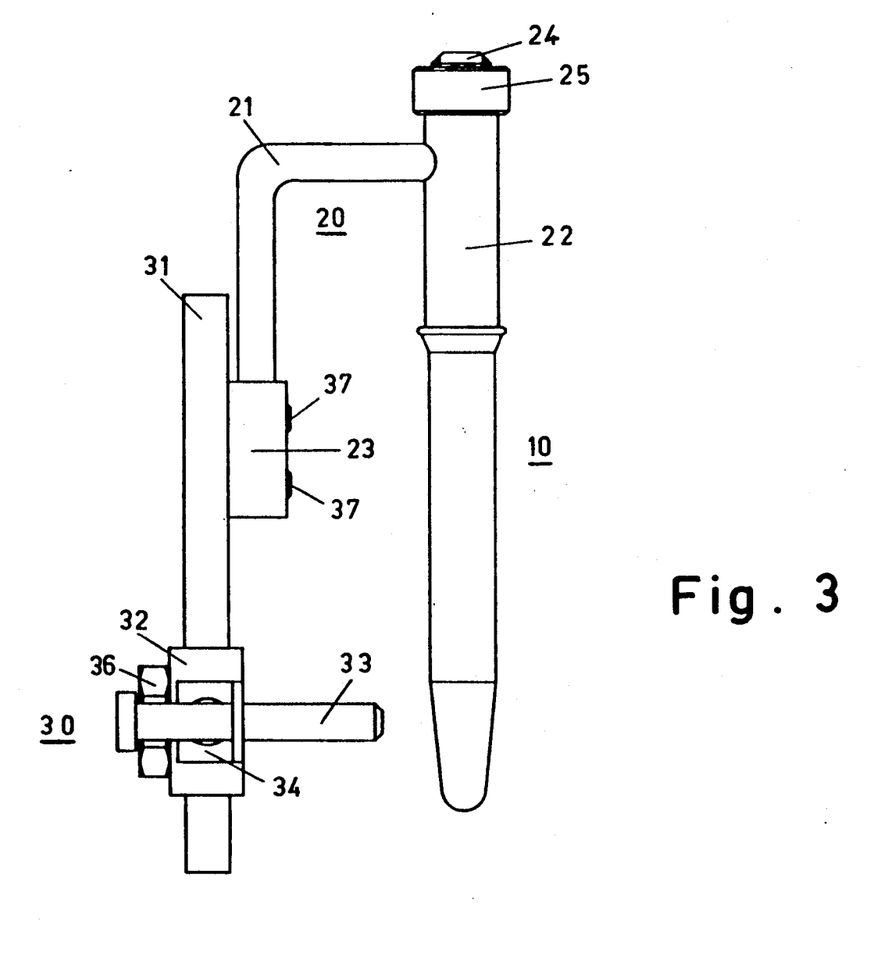
FIG. 3 is a view in side elevation of a device according to the invention, in assembled state.

The bolt 24 has at its front end a conical threaded segment 26 that corresponds with the internal threading of the conical socket of attachment means 12. At its back end, the conical bolt 24 has a semi-circular threaded segment 27, whose threads correspond with the internal threading of a hand nut 25.

For the attachment of frame 20 to the proximal end of manipulative intramedullary pin 10, the front threaded segment 26 of bolt 24 is screwed into the internal threading of the conical socket of attachment mean 12 of manipulative intramedullary pin 10. The leg 22 of frame 20, which is formed as a hollow cylinder, is pushed over the semi-circular threaded segment 27 of the conical bolt 24, and is fixed with the hand nut 25, in order to prevent axial slippage of the hollow cylinder. This immobilization is particularly important, since the holes 28 in the frame 20 must accord precisely with the locking holes of the intramedullary pin to be implanted later.

The drill jig 30 consists of a longitudinal bar 31, a slide 32 that is attached to the longitudinal bar 31 in such manner that it can be slid longitudinally, and a jig bushing 33 that is positioned sideways in a housing 34 on the slide 32 and can be rotated. Longitudinal bar 31 has attachment means 37 for separable attachment in transverse holes or channels 28 in the drill-jig leg 23 of frame 20.

Viewing the device from the tip of intramedullary pin 10, as illustrated in FIG. 2, the jig bushing 33 is oriented in such manner that it extends lengthwise and tangentially to the medullary pin 10. Slide 32 can be fixed on longitudinal bar 31 by means of a locking nut 36. The rotatable housing 34 of jig bushing 33 can be fixed on slide 32 by means of locking nut 35. After complete assembly of all parts, the device according to the invention is as illustrated in FIG. 3.

Figure 4:
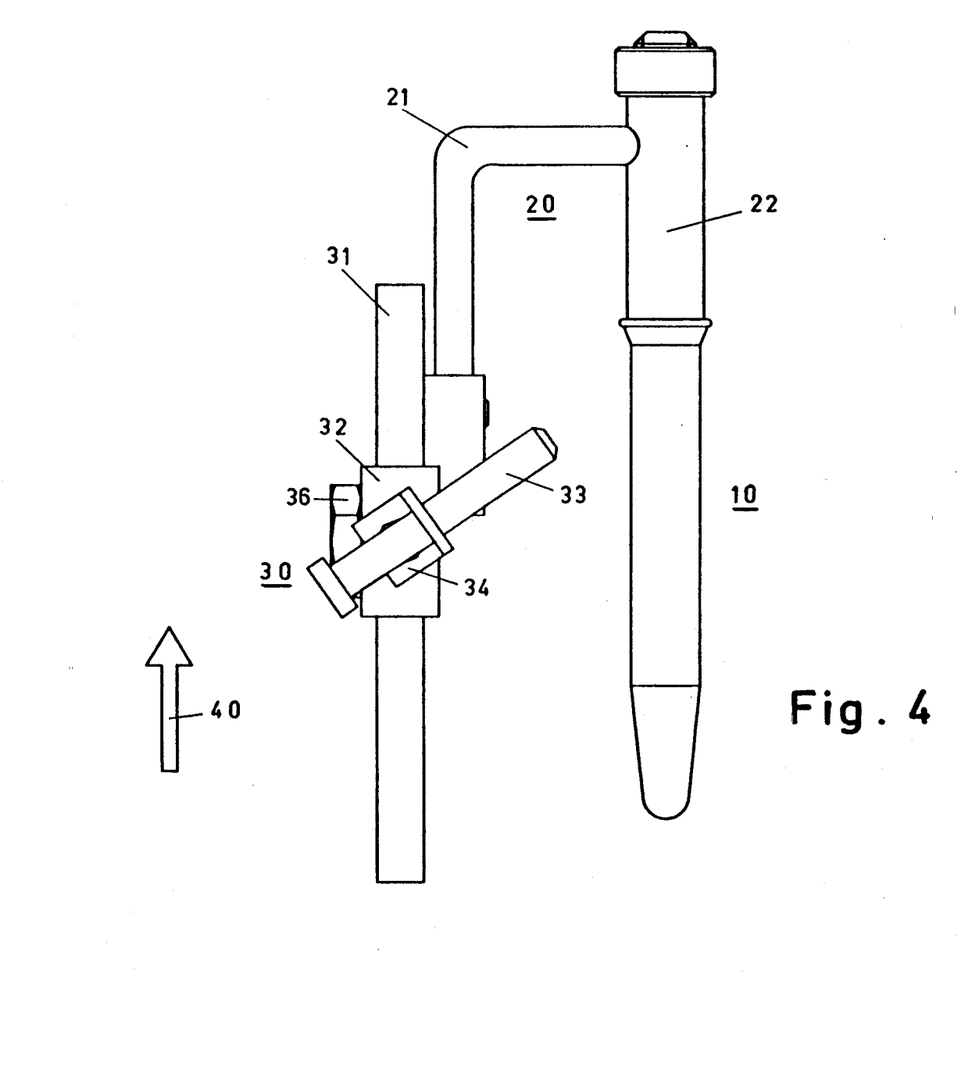
FIG. 4 is a view in side elevation of the device of FIG. 3 with the drill jig swivelled upwardly.

As shown in FIG. 4, by loosening the locking nut 36, jig bushing 33 with its rotatable housing 34 can be slid, for example, out of the position of FIG. 3 in the direction of arrow 40 along the longitudinal bar 31 into any desired position, for example the position as shown in FIG. 4, and there it can be fixed by tightening locking nut 36.

Figure 5:
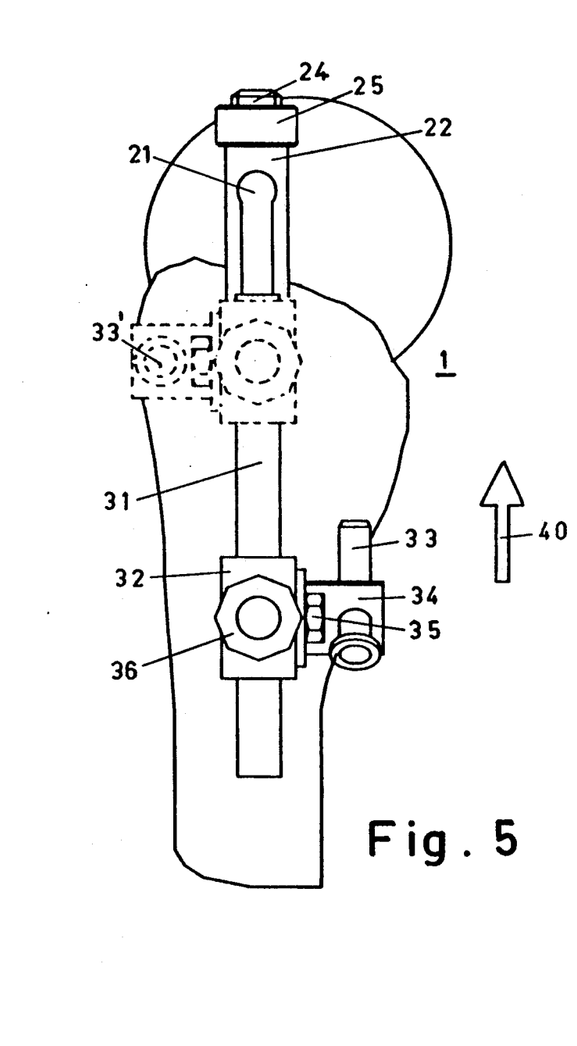
FIG. 5 is a view in front elevation view of a device according to the invention, on a femur, showing two different positions of the drill jig.
Figure 6:
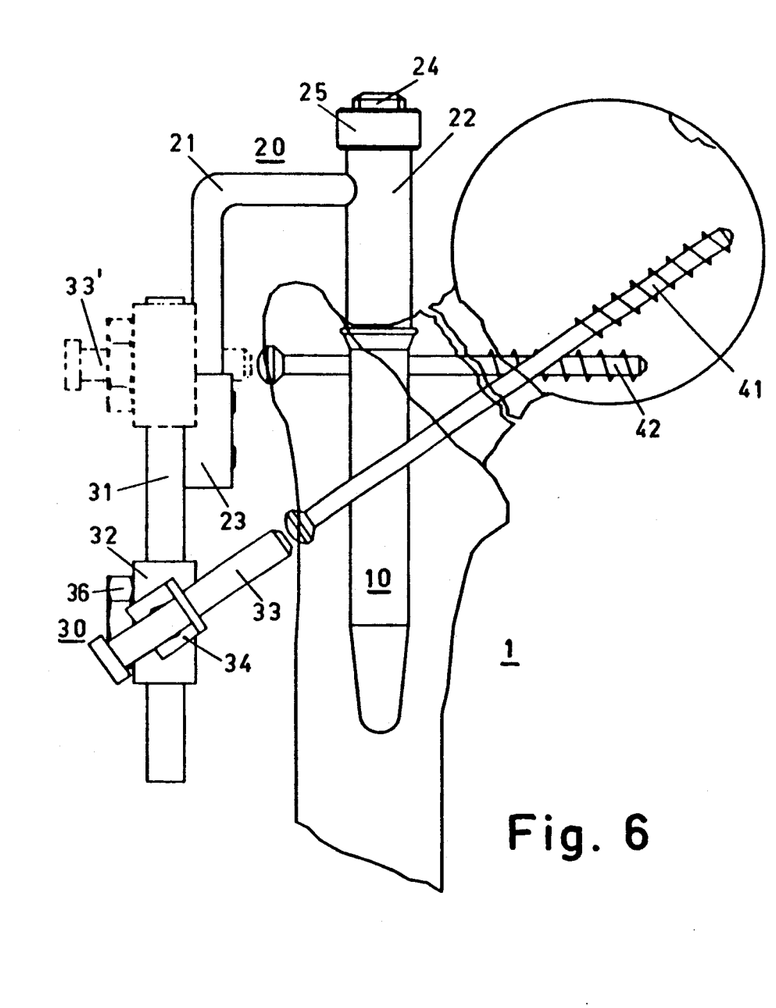
FIG. 6 is a side elevational view of the device according to the invention, as shown also in FIG. 5.

FIGS. 5 and 6 show how, by means of an instrument according to the invention, two bone screws 41 and 42 can be set in two consecutive steps. By means of the inclined jig bushing 33, a bone screw 41 can be set forward of the medullary pin 10 in the femur head. After loosening the locking nut 36, the jig bushing 33 can be moved proximally by sliding slide 32 in the direction of arrow 40, and can be fixed again at that point by tightening locking nut 36. The direction of jig bushing 33 can be adjusted by loosening and retightening the locking nut 35 as required (here it is shown perpendicular to medullary pin 10).

The position of jig bushing 33', as moved, is shown by the broken lines in FIGS. 5 and 6. In the new position of the jig bushing 33', a second bone screw 41 can be set posterior to medullary pin 10 in the femur head.

Figure 7:
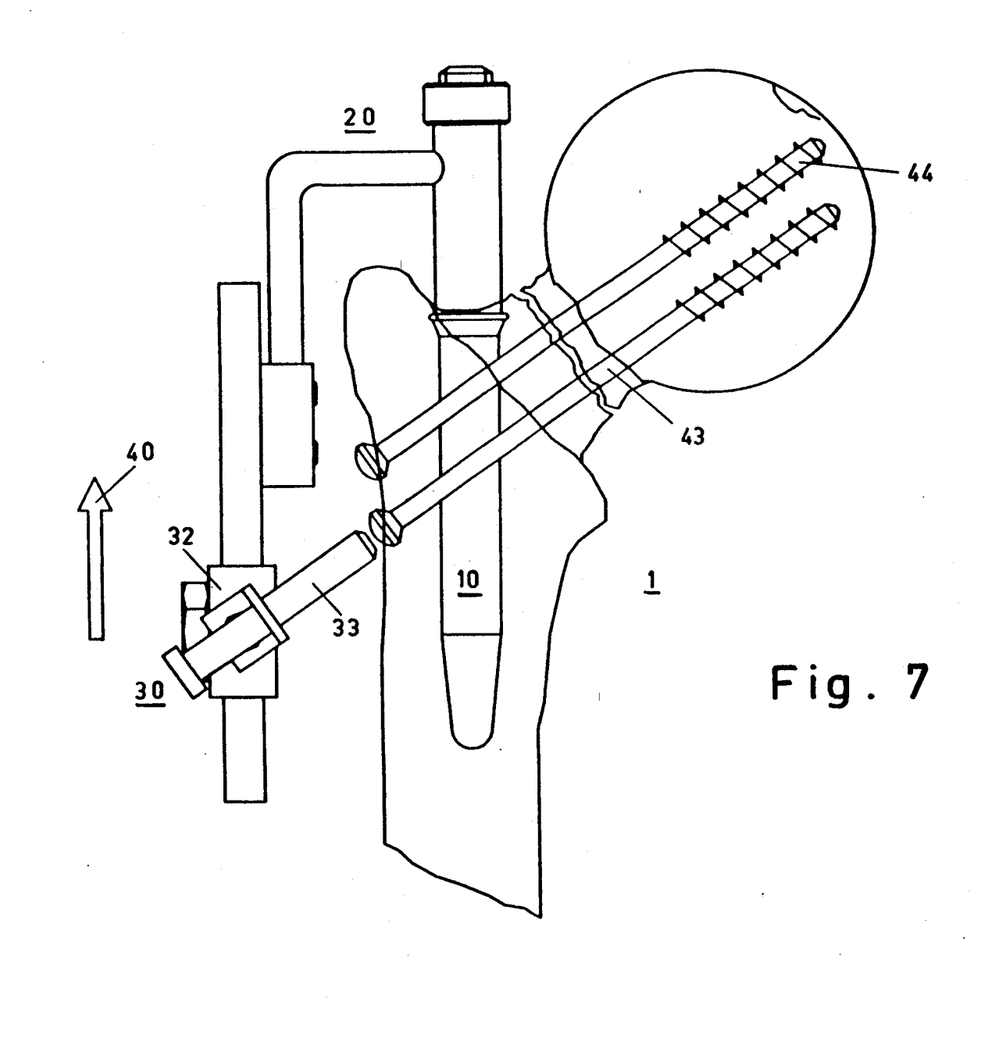
FIG. 7 is a side elevational view of a device according to the invention, on the femur, as used for the installation of two parallel bone screws.

FIG. 7 shows how, when the slide 32 is slid in the direction of arrow 40, and the inclination of jig bushing 33 remains the same, two bone screws 43 and 44 can be set in parallel at a predetermined distance from each other. Such parallel position of bone screws 43 and 44 permits maximum compression of the femur-neck fracture.

Figure 8:
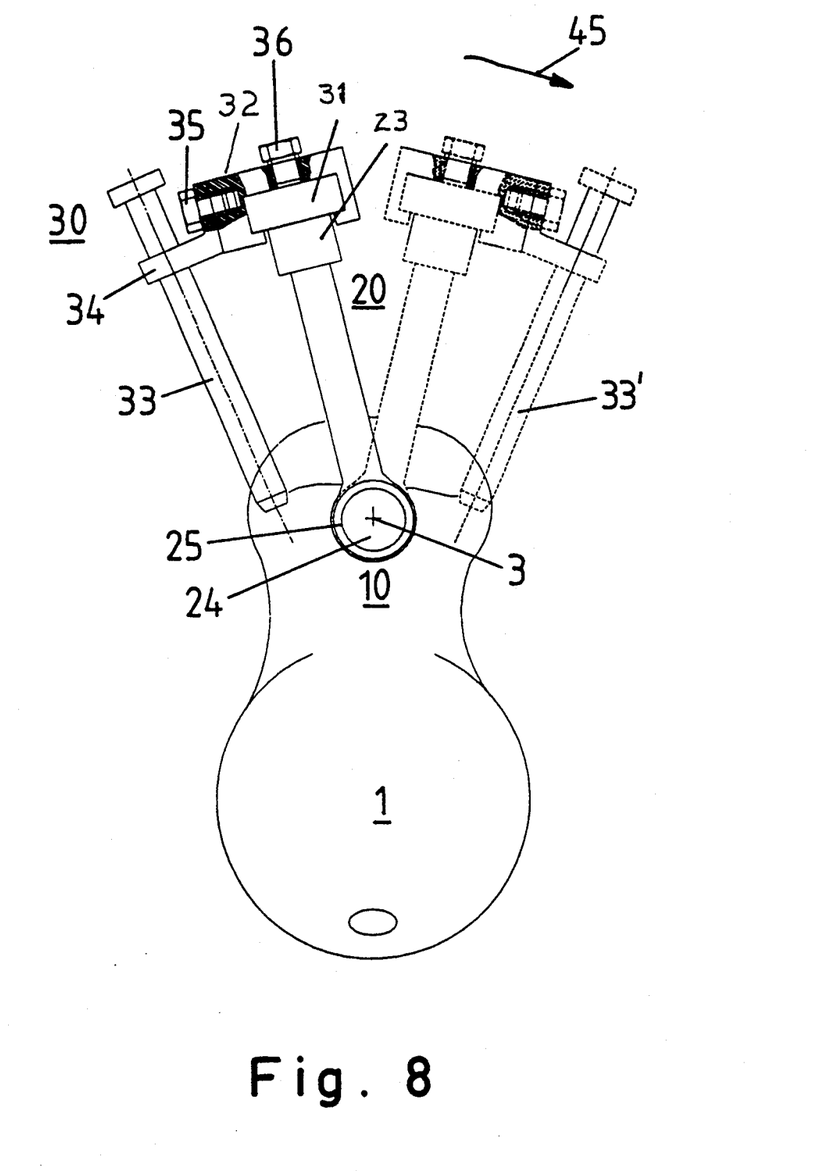
FIG. 8 is a top plan view of a device according to the invention, on the femur, with two different positions of the drill jig.

FIG. 8 is an illustration of how the instrument according to the invention can be swiveled on the medullary pin 10 axis, which coincides with the longitudinal axis 3 of medulla 2, in the direction of arrow 45. If at the same time the orientation of slide 32 is turned by 180°, the jig-bushing in the position 33' illustrated by the broken line is achieved. In this way it is possible to insert bone screws anterior or posterior to the intramedullary pin 10.

Figure 9:
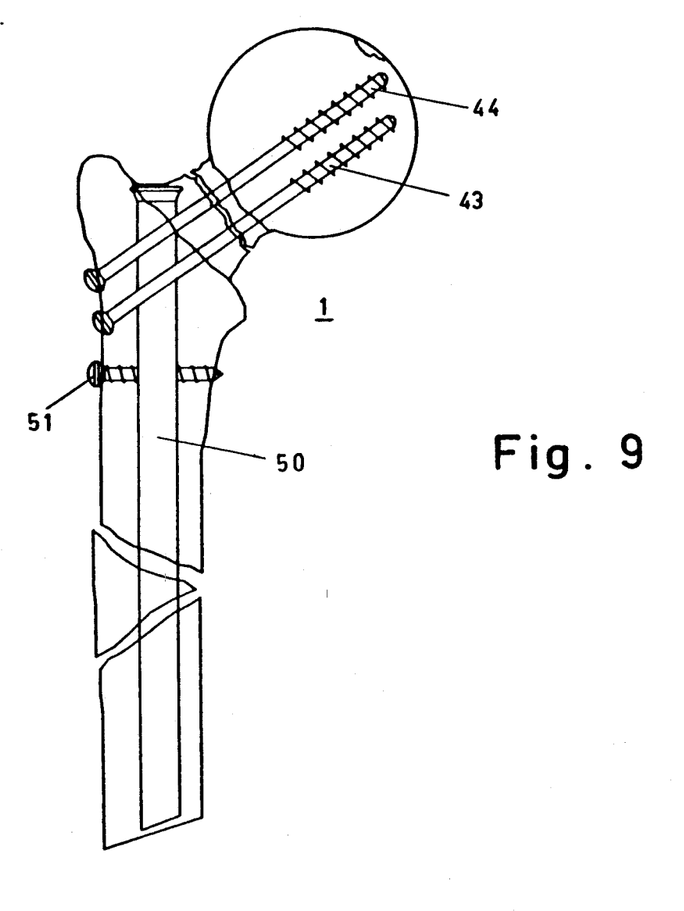
FIG. 9 is a schematic front elevational view, showing a completed osteosynthesis on the femur, as made using a device according to the invention.

Finally, FIG. 9 illustrates a completed osteosynthesis, in which two parallel draw-in bolts 43, 44, are set in the head of femur 1. Manipulative intramedullary pin 10 is replaced by a permanent intramedullary pin 50, which is locked proximally with a screw 51.

The operational technique in treating a femur fracture with use of the surgical instrument according to the invention is described briefly below.

The medulla 2 of femur 1 is opened in the Fossa piriformis area, and manipulative intramedullary pin 10 is pushed into medulla 2 of femur 1. Since intramedullary pin 10 is small, medulla 2 does not have to be enlarged. Intramedullary pin 10 is inserted with the help of frame 20, which lies laterally outside the body. The sam frame 20 will later be used for the setting of the true intramedullary pin. In addition to the insertion function, frame 20 will be used as a target device for the setting of a proximal locking screw 51 through the implanted intramedullary pin 50. The holes 28 provided for this purpose in the drill-jig leg 23 of impact frame 21 can at the same time be used for the assembly of drill jig 30. Referring to FIG. 2, jig bushing 33 of drill jig 30 is oriented in such manner that it aims lengthwise tangentially alongside manipulative intramedullary pin 10. The offset, or tangential distance, can be varied depending on the diameter of medullar pin 50 that is to be inserted later. Normally, this tangential distance is chosen in such manner that the screw set in through jig bushing 33 rests as closely as possible against the medullar pin 50 to be set in later.

Since the jig bushing 33 is housed rotatably, the screws can be set in any desired direction. In addition to the freedom of angle, the screw position can be adjusted distally or proximally, without interim stages. Depending on the anatomical conditions, the screws can be set in anterior or posterior to the pin. The optimum fracture compression can be achieved through parallel emplacement of the screws. The device according to the invention makes this very simple, since the degrees of freedom of the device can be individually fixed (e.g., the screw angle can be adjusted and the slide 32 can be locked on longitudinal bar 31). After the screw has been set in, the slide 32 is loosened and is slid distally or proximally and once again locked.

The jig bushing 33 may have, for example, an exterior diameter of 11 mm and an interior diameter of 8 mm. In addition to guiding the various drilling instruments and the screw during the setting operation, the jig bushing 33 serves at the same time as a sleeve for protecting the tissues, since, depending on indication and soft parts relationship, the screws are set through a puncture incision. To facilitate the placing of jig bushing 33 through the incision onto the bone, preferably a trocar (not shown) is used, the exterior diameter of which corresponds to the interior diameter of jig bushing 33. The trocar is then removed and is replaced by an intermediate jig bushing (not shown in the illustration), the exterior diameter of which intermediate jig bushing is the same as the interior diameter of jig bushing 33, in the example, 8 mm. The interior diameter of this intermediate inserted jig bushing varies, depending on the minor diameter needed for the inserted screw.

After the core hole has been drilled, the inserted intermediate jig bushing is removed. The necessary screw length is measured, and the screw is inserted, by the jig bushing 33.

When the screws are set in, the drill jig 30 and the manipulative intramedullary pin 10 are removed. The true intramedullary pin 50 can now be put in to replace the manipulative intramedullary pin 10. Depending on the situation, the medulla 2 must first be drilled to the desired diameter. Depending on the fracture situation, intramedullary pin 50 can be secured by additional locking screws such as 51 inserted crossways to its longitudinal axis, which locking screws can be set in with the help of the instrument according to the invention.

In hospitals it can happen that a femur-neck fracture is overlooked and that the surgeon recognizes it only during normal medullary nailing. In such a case, even after medullary nailing has been completed, the device according to the invention can be mounted on the already implanted intramedullary pin 50, and the femur neck fracture can be secondarily immobilized by means of bolts such as 43, 44. However, this procedure should be used only in an emergency, since there is a danger of a disruption of circulation in the femur head through the earlier marrow nailing.

What is claimed is:

1. Surgical instrument for positioning osteosynthetic elements comprising a U-shaped frame having a first leg and a second leg, said first leg comprising anchoring means for attaching said frame to a medullary pin at a predetermined position relative to said frame and a drill jig attached to said second leg, said drill jig having a drill bushing extending without intersecting the longitudinal axis of a medullary pin attached by said anchoring means to said first leg in said predetermined position.

2. The instrument claimed in claim 1, characterized by the fact that the frame includes an impact frame.

3. The instrument claimed in claim 1, wherein said anchoring means is adapted for coaxial and separable connection with a medullary pin.

4. The instrument claimed in claim 1, wherein the frame is adapted for connection with a temporary manipulative medullary pin inserted into a medulla.

5. The instrument claimed in claim 1, wherein the first leg is parallel to the second leg.

6. The instrument claimed in claim 1, wherein said second leg has a hole for attaching the drill jig.

7. A manipulative medullary pin having a distal end for insertion into the medulla of a bone and a proximal end, said proximal end having means for separable attachment to the instrument claimed in claim 1.

8. The instrument claimed in claim 1, wherein the second leg of said frame comprises a transverse channel having an axis substantially perpendicular to said first leg, and adapted to act as a guide for a transverse retaining screw in a medullary pin connected to said first leg.

9. A system for the treatment of fractures of the neck and shaft of a femur comprising a frame having a first leg and a second leg substantially parallel to said first leg, a pin for insertion into the medulla of the femur to be treated, means for connecting said first leg to said pin, a drill jig and means for connecting said drill jig to said second leg, said drill jig having a bushing extending without intersecting the longitudinal axis of pin when said pin is connected to said first leg.

10. The system claimed in claim 9, wherein said means for connecting said first leg to said pin comprises a cylindrical sleeve connected to said leg, a bolt positioned in said sleeve and means for connecting one end of said bolt to said pin.

11. The system claimed in claim 10, wherein said bolt has a threaded conical end and said pin has a threaded socket for receiving the conical threaded end of said bolt.

12. A method for treating fractures of the neck and shaft of the femur which comprises inserting a manipulative pin in the medulla of the femur, attaching a U-shaped frame having two parallel legs to said pin by attaching a first leg coaxially to said pin, attaching a drill jig to the second leg of said frame, inserting a screw by means of said drill jig through the neck and into the head of the femur without intersecting the longitudinal axis of said pin, withdrawing the manipulative pin from the medulla, and inserting a treatment pin into the medulla.

13. The method claimed in claim 12 and comprising inserting a retaining screw transverse to said treatment pin after said pin has been introduced into the medulla.

14. Surgical instrument for positioning osteosynthetic elements comprising a U-shaped frame having a first leg and a second leg, said first leg comprising a hollow cylinder, anchoring means at said first leg for attachment to a medullary pin and a drill jig attached to said second leg, said drill jig having a drill bushing positioned to extend tangentially to a medullary pin attached by said anchoring means to said first leg, said anchoring means comprising a conical bolt having a front threaded segment, a rear threaded segment and a nut, said nut having threads matching the threads on said rear segment, said conical bolt being adapted to be inserted through said hollow cylinder, and by means of said nut and said threaded segments separably connected with a medullary pin.

15. Surgical instrument for positioning osteosynthetic elements comprising a U-shaped frame having a first leg and a second leg, anchoring means at said first leg for attachment to a medullary pin and a drill jig attached to said second leg, said drill jig comprising a longitudinal bar, means connecting said bar to said second leg, a slide positioned to slide longitudinally on said bar and a drill bushing rotatably mounted on said slide and positioned to extend tangentially to a medullary pin attached by said anchoring means to said first leg.

16. A system for the treatment of fractures of the neck and shaft of a femur comprising a frame having a first leg and a second leg substantially parallel to said first leg, a pin for insertion into the medulla of the femur to be treated, means for connecting said first leg to said pin, a drill jig, connecting means for connecting said drill jig to said second leg, said connecting means comprising a bar, a slide displaceable along said bar, means for rotatably mounting said jig on said slide and means connecting said bar to said second leg, said drill jig also having a bushing extending tangentially to said pin when said pin is connected to said first leg.

* * * * *